US012635874B2

(12) United States Patent
Dovgal et al.

(10) Patent No.: US 12,635,874 B2
(45) Date of Patent: May 26, 2026

(54) METHOD FOR THE INSPECTION OF AN OPHTHALMIC LENS FOR SEMI-OPAQUE DEFECTS

(71) Applicant: Alcon Inc., Fribourg (CH)

(72) Inventors: Vladimir Dovgal, Frankfurt (DE); Sandra Kraus, Niedernberg (DE)

(73) Assignee: Alcon Inc., Fribourg (CH)

( * ) Notice: Subject to any disclaimer, the term of this patent is extended or adjusted under 35 U.S.C. 154(b) by 1087 days.

(21) Appl. No.: 17/648,059

(22) Filed: Jan. 14, 2022

(65) Prior Publication Data

US 2022/0233071 A1 Jul. 28, 2022

Related U.S. Application Data

(60) Provisional application No. 63/141,544, filed on Jan. 26, 2021.

(51) Int. Cl.
*A61B 3/117* (2006.01)
*A61B 3/00* (2006.01)

(52) U.S. Cl.
CPC .......... *A61B 3/1173* (2013.01); *A61B 3/0008* (2013.01)

(58) Field of Classification Search
CPC . A61B 3/0008; A61B 3/1173; G01M 11/0278
See application file for complete search history.

(56) References Cited

U.S. PATENT DOCUMENTS

| | | | |
|---|---|---|---|
| 5,627,638 A | 5/1997 | Vokhmin | |
| 2002/0163638 A1 | 11/2002 | Biel et al. | |

| | | | |
|---|---|---|---|
| 2006/0098190 A1 | 5/2006 | Miyake et al. | |
| 2015/0253456 A1 | 9/2015 | Norton | |
| 2017/0011507 A1 | 1/2017 | Wong et al. | |
| 2018/0024077 A1 | 1/2018 | Tonn | |
| 2019/0257714 A1 | 8/2019 | Schneider et al. | |

(Continued)

FOREIGN PATENT DOCUMENTS

| | | |
|---|---|---|
| CA | 2413343 A1 | 6/2004 |
| CN | 108982072 A | 12/2018 |
| DE | 102015201823 A1 | 8/2016 |

(Continued)

OTHER PUBLICATIONS

International Search Report and Written Opinion dated Apr. 26, 2022 for International Application No. PCT/IB2022/050648.

*Primary Examiner* — Jack Dinh
(74) *Attorney, Agent, or Firm* — Patterson + Sheridan, LLP

(57) ABSTRACT

A method for inspecting an ophthalmic lens for the presence of an unacceptable semi-opaque defect in a lens body thereof comprises the steps of: illuminating the lens body with laser light in an area bounded by an edge of the lens body; detecting the intensity of laser light scattered by the illuminated lens body in a predetermined detection direction which is different from a direction of reflection; comparing the detected intensity of the scattered laser light with a predetermined threshold intensity; determining a size of at least one coherent area in which the detected intensity of the scattered laser light is higher than the predetermined threshold intensity; determining whether the size of the at least one coherent area is larger than a predetermined threshold size, and rejecting the ophthalmic lens in case the size of the at least one coherent area is larger than the predetermined threshold size.

12 Claims, 2 Drawing Sheets

(56)           References Cited

U.S. PATENT DOCUMENTS

2019/0323920 A1    10/2019  Smorgon et al.

FOREIGN PATENT DOCUMENTS

| | | | |
|---|---|---|---|
| EP | 0605990 | A2 | 7/1994 |
| EP | 1248092 | A2 | 10/2002 |
| ES | 2143944 | A1 | 5/2000 |
| JP | S6070334 | A | 4/1985 |
| JP | H0229877 | A | 1/1990 |
| JP | H10152414 | A | 6/1998 |
| JP | 2003-057611 | A | 2/2003 |
| JP | 2003-090805 | A | 3/2003 |
| JP | 2004095792 | A | 3/2004 |
| JP | 2004-212353 | A | 7/2004 |
| JP | 2005-249489 | A | 9/2005 |
| JP | 2010197352 | A | 9/2010 |
| JP | 2016-016407 | A | 2/2016 |
| JP | 2017146581 | A | 8/2017 |
| WO | 9501558 | A1 | 1/1995 |

METHOD FOR THE INSPECTION OF AN OPHTHALMIC LENS FOR SEMI-OPAQUE DEFECTS

CROSS REFERENCE TO RELATED APPLICATIONS

This application claims priority to U.S. Provisional Application No. 63/141,544, filed Jan. 26, 2021, the entire contents of which are incorporated herein by reference.

FIELD

The present disclosure deals with systems and methods for the inspection of an ophthalmic lens for the presence of an unacceptable semi-opaque defect. The entire contents of this application are hereby incorporated by reference in their entirety.

BACKGROUND

Ophthalmic lenses such as intraocular lenses are inspected, among others, for the presence of unacceptable cosmetic defects prior to being delivered to the customers. An intraocular lens typically comprises a lens body that is bounded by an edge, and two haptics attached to the lens body. In particular, the lens body must be carefully inspected for the presence of unacceptable cosmetic defects, as the lens is subsequently implanted in the user's eye (e.g. during cataract surgery). Inspection of the lens body of an intraocular lens for unacceptable cosmetic defects is often performed by experienced operators, even when using automated lens inspection equipment for capturing images of the intraocular lens and image analysis of the captured images.

Cosmetic defects of intraocular lenses comprise cosmetic defects (e.g. inclusions, bubbles, small particles, etc.) which are well-visible during the inspection under conventional illumination conditions (e.g. in a dark-field illumination configuration using incoherent visible light), and also comprise cosmetic defects which are normally practically invisible under conventional illumination conditions. The latter cosmetic defects are often called 'semi-opaque' defects, and can be detected—if at all—by very experienced operators only.

However, these latter defects—although occurring in very rare instances only—should also be reliably detected as they may adversely affect the user's vision. For example, a semi-opaque cosmetic defect that may occur in intraocular lenses is an orange peel texture on the surface of the lens body, while another semi-opaque defect is haze (like a kind of a decent cloudy portion in the lens body). As mentioned, such semi-opaque defects occur very rarely only, however, they are not easy to detect even by very experienced operators.

It is therefore an object of the instant disclosure to provide systems and methods that overcome the afore-mentioned disadvantages and allow for the reliable detection of unacceptable semi-opaque defects.

SUMMARY

In certain embodiments, the present disclosure provides a method for inspecting an ophthalmic lens, in particular an intraocular lens, for the presence of an unacceptable semi-opaque defect in a lens body thereof, and comprises the steps of: illuminating the lens body of the ophthalmic lens, in particular the intraocular lens, with laser light in an area bounded by an edge of the lens body; detecting the intensity of laser light scattered by the illuminated lens body in a predetermined detection direction which is different from a direction of reflection of the illuminating laser light; comparing the detected intensity of the scattered laser light with a predetermined threshold intensity; determining a size of at least one coherent area in which the detected intensity of the scattered laser light is higher than the predetermined threshold intensity; determining whether the size of the at least one coherent area is larger than a predetermined threshold size, and rejecting the ophthalmic lens due to containing a semi-opaque defect in the lens body in case the size of the at least one coherent area is larger than the predetermined threshold size.

In accordance with certain aspects of the present disclosure, the step of comparing the detected intensity of the scattered laser light with a predetermined threshold intensity may be performed by: converting the detected intensity of the scattered laser light to a detected grey scale value representative of the detected intensity of the scattered laser light; converting the predetermined threshold intensity to a threshold grey scale value representative of the predetermined threshold intensity, and comparing the detected grey scale value with the threshold grey scale value; and the step of determining whether the size of the at least one coherent area is larger than a predetermined threshold size may be performed by: determining the size of at least one coherent area in which the grey scale values are above the threshold grey scale value.

In accordance with further aspects of the present disclosure, a laser diode may be used for illuminating the lens body of the ophthalmic lens.

In accordance with still further aspects of the present disclosure, the step of illuminating the lens body may comprise illuminating the lens body with a laser beam impinging on the surface of the lens body only within the bounds of the edge of the lens body, with the laser beam having a stationary impingement profile covering an area of at least 80% of the area of the surface of the lens body.

In some embodiments of the present disclosure, the laser beam may be collimated with an evenly distributed intensity, and the stationary impingement profile may be a circular profile having a diameter that is 5%-10% smaller than the diameter of the edge bounding the lens body.

In some further embodiments of the present disclosure, the stationary impingement profile of the laser beam may have the shape of a grid with rectangularly arranged grid lines, with an evenly distributed intensity along the grid lines.

In accordance with yet further aspects of the present disclosure, the step of illuminating the lens body may comprise illuminating the lens body with a laser beam having an impingement profile on the surface of the lens body, the impingement profile covering an area of less than 20% of the area of the surface of the lens body, and the impingement profile may be moved over the surface of the lens body along a predetermined path to sequentially illuminate different portions of the lens body.

In some embodiments of the present disclosure, the beam may be focused and the impingement profile may be a circular spot, and the circular spot may be moved over the surface of the lens body along the predetermined path.

In some further embodiments of the present disclosure, the impingement profile a straight line, and the straight line may be moved over the surface of the lens body along the predetermined path, the predetermined path being normal to the straight line of the impingement profile.

The methods provided by the present disclosure have several advantages. First of all, they are objective methods, since the determination of whether or not an ophthalmic lens is to be rejected due to containing a semi-opaque defect in the lens body is made based on measurements and automatic evaluation of measurement results obtained by technical equipment and machine algorithms without any subjective determination of a human operator. This leads to a consistent interpretation of the measurement results and eliminates any subjective interpretation by a human operator. Second, the use of laser light (coherent light of higher intensity) for illumination of the ophthalmic lens to be inspected results in semi-opaque defects becoming visible which have hitherto been invisible due to their intensity being too low to be noticed/detected. Advantageously, the illuminating laser light is monochromatic although this is not a requirement. In case of monochromatic laser light, a detector detecting any laser light scattered by a semi-opaque defect towards the detector must only be sensitive at the wavelength of the monochromatic light (or within a very narrow band around the central—monochromatic—wavelength) so that stray light (scattered light) having wavelengths different from that of the monochromatic laser light can be blocked/filtered so that is not detected by the detector, thus increasing the signal-to-noise ratio at the detector. Third, the detector detecting the intensity of the (preferably monochromatic) scattered laser light is arranged to only detect light scattered in a predetermined detection direction different from the direction of reflection of the laser light. Accordingly, laser light reflected by the ophthalmic lens does not adversely affect the intensity measurement at the detector since reflected laser light does not impinge onto the detector. Or to say it on other words, inspection of the ophthalmic lens is performed in a dark-field illumination configuration.

It is noteworthy that haze—representing a specific kind of semi-opaque defect that should be identified by the method according to the present disclosure—typically manifests itself as a kind of 'cloudy' volume within the lens body of the ophthalmic lens, and the (typically two-dimensional) detectors (e.g. CCD detectors) are detecting the laser light scattered by such volumetric semi-opaque defects as a coherent area in which the detected intensity of the scattered laser light (at any location within such coherent area) is higher than a predetermined threshold intensity. And if this coherent area in which the detected intensity of scattered light is higher than the predetermined threshold intensity is larger than a predetermined threshold size, it is determined that the ophthalmic lens is to be rejected due to containing a semi-opaque defect in the lens body.

With respect to an automatic determination as to whether or not the lens body of the ophthalmic lens contains a semi-opaque defect (e.g. haze), the detected intensity of the scattered laser light may be converted into a detected grey scale value, and the predetermined threshold intensity is also converted to a threshold grey scale value. In such instance, the detected grey scale values are compared with the threshold grey scale values, and in case the size of a coherent area in which the grey scale values are above the threshold grey scale value, the ophthalmic lens is rejected.

The use of a laser diode for illuminating the ophthalmic lens to be inspected is advantageous as laser diodes are small and comparatively inexpensive components which are readily available on the market.

Generally, it is possible to illuminate the lens body with a laser beam having an impingement profile on the (illuminated) surface of the lens body that is stationary and is only within the bounds of the edge of the lens body, while at the same time covering an area of at least 80% of the area of the surface of the lens body. The laser beam impinging on the surface of the lens body (at least partially) enters the lens body through the (illuminated) surface and is scattered by the semi-opaque defect, if present. 'Within the bounds of the edge of the lens body' means that the edge itself is not impinged upon by the laser beam, as the edge is known for generating quite a lot of unwanted stray light (scattered light) at the detector that is not caused by a semi-opaque defect. 'Impingement profile' is intended to denote the geometrical shape of the area on the surface of the lens body actually impinged upon by the laser beam. 'Stationary' means that the area on the surface of the lens body impinged upon by the laser beam does not change position during measurement/determination (it is always the same area that is impinged upon by the laser beam during the measurement/determination).

For example, the beam may be a collimated laser beam with an evenly distributed intensity, and the stationary impingement profile may be a circular profile. This means that on the surface of the ophthalmic lens the laser beam is bounded by a circle, while the intensity is the same over the area bounded by the circle. The circular impingement profile advantageously may have a diameter which is 5% to 10% smaller than the diameter of the (circular) edge bounding the lens body.

Alternatively, the impingement profile of the laser beam may have the shape of a grid with rectangularly arranged grid lines, and the intensity may be evenly distributed along these rectangularly arranged grid lines. The mesh size of the individual cells of such grid bounded by the rectangularly arranged grid lines is to be chosen sufficiently small so as to be able to reliably detect the semi-opaque defect. In any event, the overall size of the stationary impingement profile (i.e. the outer boundary of the laser beam on the surface of the lens body) is chosen such that those portions of the lens body in which the semi-opaque defects may be present and may influence the user's vision are located within the impingement profile.

Generally, it is also possible to illuminate the lens body with a laser beam having an impingement profile on the surface of the lens body, the impingement profile covering an area of less than 20% of the area of the lens body, and to move the said impingement profile over the lens body along a predetermined path so as to sequentially illuminate different portion of the lens body. Such predetermined path may be selected in accordance with the impingement profile of the laser beam. For example, the impingement profile may be a circular spot (meaning that the illuminated spot on the surface of the lens body is bounded by a circle) and the predetermined path may comprise one or more circles (concentric with a central optical axis extending through the lens body) along which the spot is moved over the lens body. Alternatively, the predetermined path along which the circular spot may be moved may be a spiral, or may have any other geometrical shape. Another example for the impingement profile may be a straight line (extending across the surface of the lens body), and the predetermined path may be normal to the straight line (and may extend in a plane parallel to the 'plane' of the lens body), so that the straight line of the impingement profile is moved over the surface of the lens body like the scanning line of a scanner.

BRIEF DESCRIPTION OF THE DRAWINGS

Further advantageous aspects of the systems and methods of the present disclosure may become apparent from the following description of embodiments with the aid of the schematic drawings in which.

DETAILED DESCRIPTION

Figures 1, 2, 3, 4, 5:
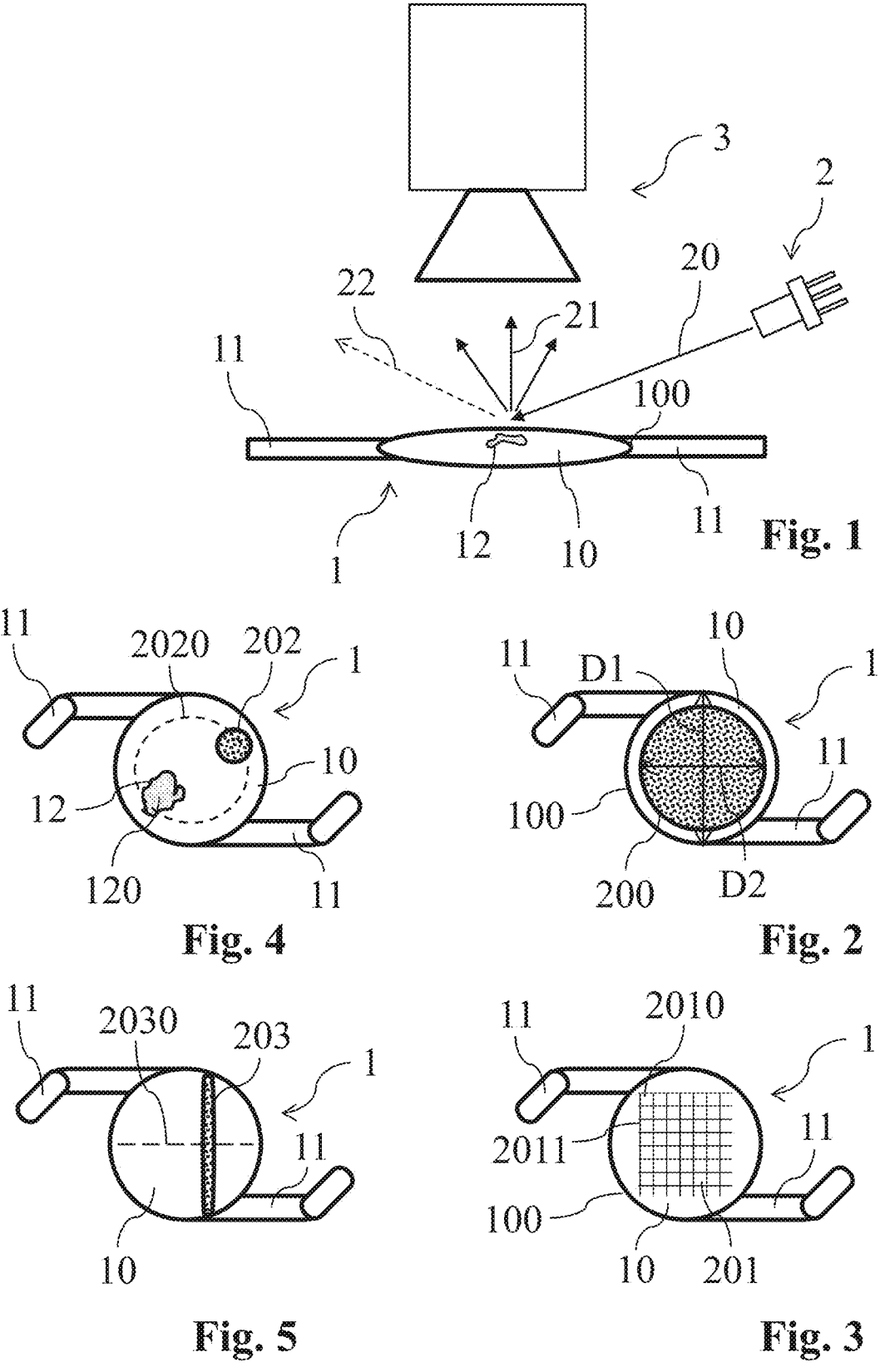
FIG. 1 shows an arrangement for performing the methods of the present disclosure, with a semi-opaque defect being contained in the lens body of the ophthalmic lens inspected, according to certain embodiments.
FIG. 2 shows an ophthalmic lens during inspection, with a stationary circular impingement profile of the laser beam impinging on the surface of the lens body, according to certain embodiments of the present disclosure.
FIG. 3 shows an ophthalmic lens during inspection, with a stationary impingement profile of the laser beam having the shape of a grid, according to certain embodiments of the present disclosure.
FIG. 4 shows an ophthalmic lens containing a semi-opaque defect in the lens body during inspection, with an impingement profile in the form of a circular spot which is moved over the surface of the lens body, according to certain embodiments of the present disclosure.
FIG. 5 show an ophthalmic lens during inspection, with an impingement profile in the form of a straight line which is moved over the surface of the lens body, according to certain embodiments of the present disclosure.

FIG. 1 shows an arrangement for performing the method according certain embodiments of the present disclosure. As can be seen, an ophthalmic lens 1 to be examined, in the instant case an intraocular lens, comprises a lens body 10 and two haptics 11, as is well-known in the art. As can further be seen, the lens body 10 contains a semi-opaque defect 12 schematically indicated in FIG. 1. Lens body 10 is bounded by a circumferentially running circular edge 100 (as can also be seen in FIG. 2-FIG. 5). Lens body 10 is illuminated with laser light 20 emitted by a laser diode 2, and a camera 3 comprising a sensor (e.g. a CCD array) is arranged in a predetermined detection direction (pointing towards the camera 3) which is different from a direction of reflection (indicated by the dashed line 22) of the illuminating laser light 20. The intensity of the laser light emitted by laser diode 2 may generally be in the range of 0.5 mW/cm$^2$ to 5 mW/cm$^2$, and may in particular be about 1 mW/cm$^2$. The wavelength may generally be within the range of 400 nm to 700 nm, and may in particular be about 670 nm. A suitable laser diode may be a laser diode of the type L670VH1 available from the company Thorlabs GmbH, Münchner Weg 1, 85232 Bergkirchen, Germany.

Figure 6:
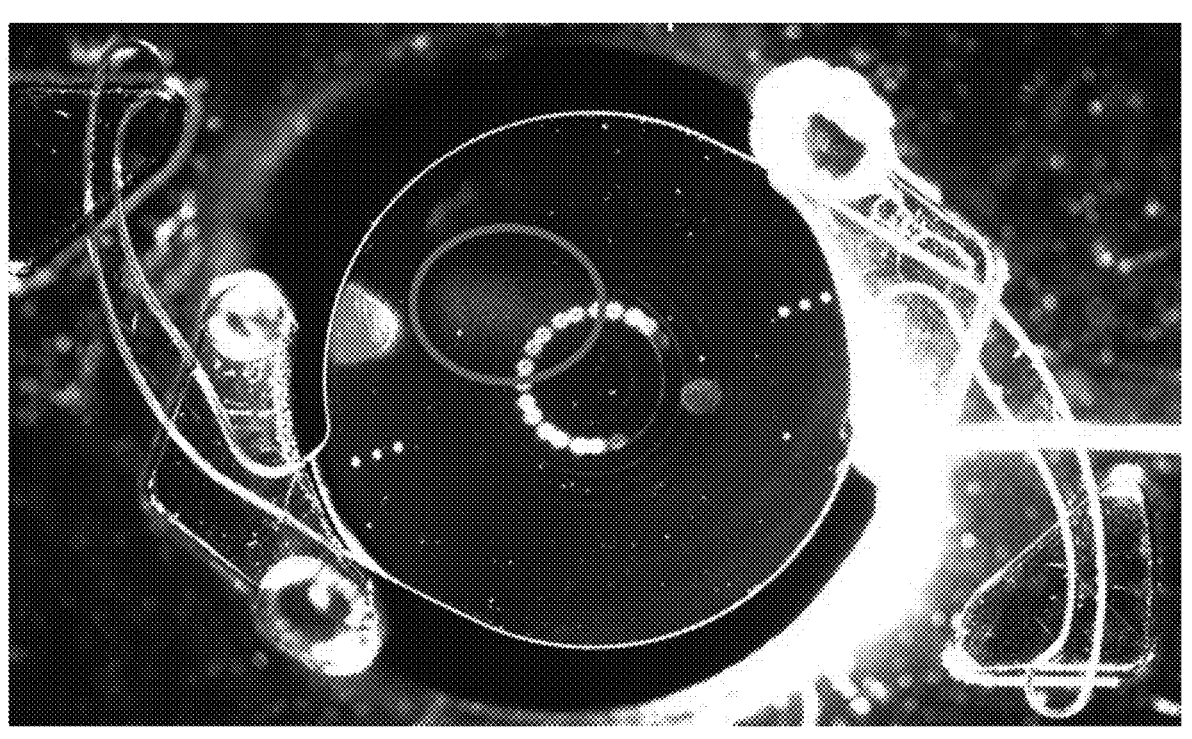
FIG. 6 shows an image of an inspected ophthalmic lens, with the lens body containing a semi-opaque defect (haze), according to certain embodiments of the present disclosure.

The arrangement shown in FIG. 1 is known as a dark-field illumination configuration, only structures scattering present in lens body 10 that scatter the illuminating laser light 20 towards camera 3 appear as bright structures in an image of lens body 10, otherwise the image of lens body 10 captured by camera 3 is dark. This means, that laser light entering into lens body 10 and being scattered by the semi-opaque defect 12 contained in lens body 10 in the predetermined detection direction (i.e. towards camera 3) can be detected by camera 3. The intensity of this scattered laser light 21 can be measured. Since the scattered laser light 21 propagating in the predetermined detection direction towards camera 3 is only a small fraction of the light scattered by semi-opaque defect 12, the intensity of this scattered laser light 21 is still comparatively low (as can be seen in FIG. 6 in the area circumscribed by the ellipse within the lens body). This scattered laser light 21 is indicative of the presence of semi-opaque defect 12.

The semi-opaque defect 12 shown is haze, with haze being a defect that is not present at the surface but is contained within the bulk material of lens body 10. Other semi-opaque defects (e.g. orange peel defects) may be present at the surface. The intensity of the scattered laser light 21 is detected by the sensor of camera 3 (e.g. CCD array), and is compared with a pre-set (predetermined) threshold intensity.

From the point of view of the sensor of camera 3 (e.g. CCD array) semi-opaque defect 12 (as shown, this defect is haze which is a volumetric defect, as it is contained in the bulk material) manifests itself as a coherent area 120 in which the detected intensity of the scattered laser light 21 is higher than the threshold intensity (see FIG. 4). And if the size of this coherent area 120 is larger than a predetermined threshold size, the ophthalmic lens 1 is rejected due to containing a semi-opaque defect. In case more than one semi-opaque defect 12 is contained in lens body 10, the sizes of the individual coherent areas 120 in which the intensity of the scattered laser light 21 is above the threshold intensity (thus being indicative of the individual semi-opaque defects 12) are summed up, and if the sum of the sizes of the individual coherent areas 120 is above the threshold size, the ophthalmic lens 1 is rejected, too.

In one embodiment, the detected intensity of the scattered laser light 21 as well as the predetermined threshold intensity are converted to grey scale values, respectively, i.e. to a detected grey scale value representative of the detected intensity of the scattered laser light 21 as well as to a threshold grey scale value representative of the predetermined threshold intensity. The determination whether the size of the coherent area representing the semi-opaque defect 12 exceeds the predetermined threshold size can then be performed by comparing the detected grey scale values with the threshold grey scale value.

In the following various different options are discussed how the ophthalmic lens 1 to be inspected, or more precisely the lens body 10 thereof, may be illuminated with laser light 20. Generally, these options can be sub-divided into options in which lens body 10 is illuminated with a laser beam that has a stationary impingement profile (i.e. a profile that does not move) and options in which lens body 10 is illuminated with an impingement profile that is moved over the surface of lens body 10. These options are discussed in the following with the aid of FIG. 2-FIG. 5.

In FIG. 2 an example is shown in which the laser light illuminates the lens body 10 only within the bounds of the circular edge 100 bounding the lens body 10, i.e. the circular edge 100 itself is not illuminated as the edge 100 is known to generate quite a lot of unwanted stray light (and the semi-opaque defect 12 is not present at the edge), according to certain embodiments of the present disclosure. In this example, the laser light 20 illuminating lens body 10 is a collimated laser beam with an evenly (i.e. uniformly) distributed intensity, with the laser beam impinging on the surface of lens body 10 having a stationary circular impingement profile 200. The circular impingement profile 200 has a diameter D2 that is 5% to 10% smaller than the diameter D1 of the edge 100 bounding lens body 10. In the example shown in FIG. 2, the diameter D2 of the circular impingement profile 200 is about 80% of the diameter D1 of the circular edge 100 of lens body 10. Illuminating the lens body in this manner allows the measurement of the intensities of the scattered light to be performed in a single measurement run.

FIG. 3 shows an example in which the laser light illuminates the lens body 10 again only within the bounds of the circular edge 100 bounding the lens body 10, according to certain embodiments of the present disclosure. However, different from the example shown in FIG. 2, the impingement profile 201 of the laser beam has the shape of a grid with rectangularly arranged grid lines 2010, 2011. Impingement profiles 201 in the form of a grid can be easily generated with the aid of diaphragms or similar components which may even be an integral part of the laser diode 2 (FIG. 1). The rectangularly arranged grid lines 2010, 2011 define a mesh with a small size of the individual cells of the mesh bounded by the grid lines 2010, 2011, in order to also allow the measurement of the intensities of the scattered laser light to be performed in a single measurement run.

Generally, the stationary impingement profile 200, 201 (regardless of whether being circular or being a grid) covers an area of at least 80% of the area of the surface of the lens body 10 in order to obtain a reliable determination as to the presence (or absence of a semi-opaque defect 12).

In FIG. 4 an example is shown in which the laser light illuminates the lens body 10 with a beam that is focused such that the impingement profile 202 is a circular spot covering an area on the surface of lens body 10 that has a size which is about one sixteenth of the size of the area of the whole surface (front or back, whichever is facing the laser beam) of lens body 10, according to certain embodiments of the present disclosure. The circular spot is moved over the surface of the lens body along a predetermined path 2020 indicated by a dashed circle in FIG. 4, whereupon the circular spot may additionally be moved along a further circle interior of and concentric with the dashed circle shown in FIG. 4, so as to cover an area of at least 80% of the area of the surface of lens body 10. In this embodiment, the measurements of the intensities of the scattered laser light are performed sequentially as the circular spot moves along the predetermined path 2020. Alternatively, the predetermined path may have the shape of a spiral, or may have any other suitable shape to cover the said area of the surface of lens body 10.

FIG. 5 shows an example in which the laser light illuminates the lens body 10 with a beam that has an impingement profile 203 which is a straight line, according to certain embodiments of the present disclosure. This straight line is moved over the surface of the lens body 10 along a predetermined path 2030 which is normal to the straight line 203, as indicated by the dashed line in FIG. 5, very similar to a scanning line that is moved over the surface of an object to be scanned. Here, too, the measurements of the intensities of the scattered laser light are performed sequentially as the impingement profile 203 moves along the predetermined path 2030.

Figure 7:
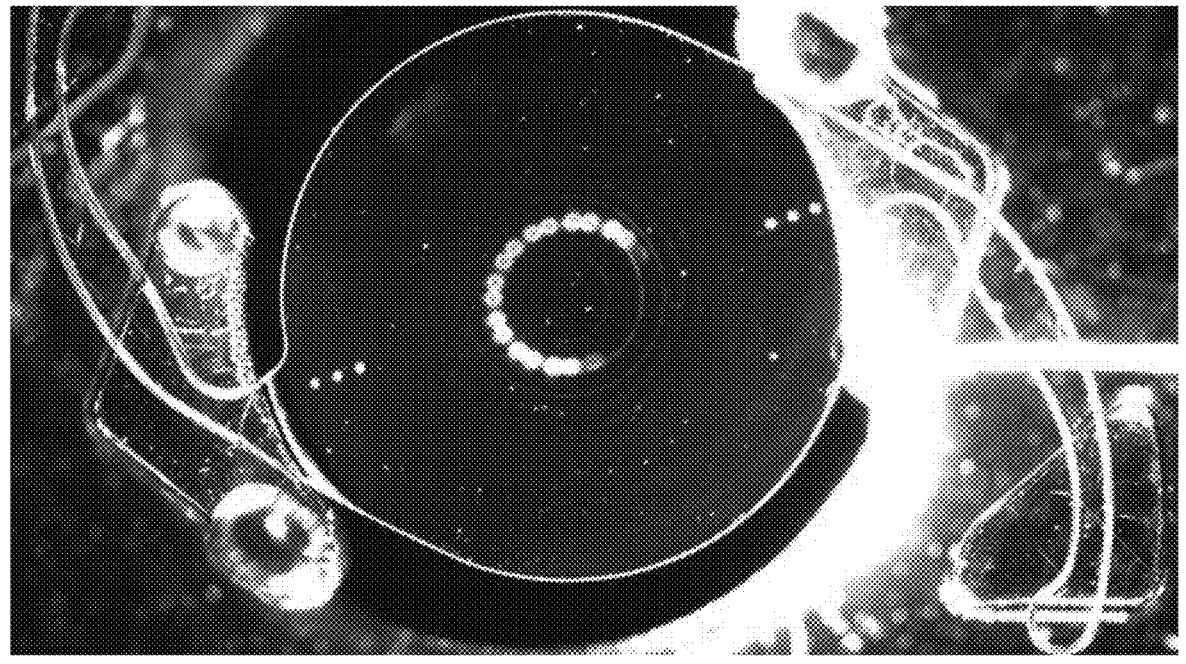
FIG. 7 shows an image of an ophthalmic lens inspected, with the lens body not containing a semi-opaque defect, according to certain embodiments of the present disclosure.

FIG. 6 shows a (dark-field) image of an ophthalmic lens—here: an intraocular lens—that comprises a semi-opaque defect (haze) in the lens body, the haze being visible within the area circumscribed by the ellipse drawn into the image, according to certain embodiments of the present disclosure. Even though laser light is used, the haze is hardly visible in the lens body but at least allows for being detected. In comparison thereto, FIG. 7 shows a (dark-field) image of an intraocular lens not containing any haze, according to certain embodiments of the present disclosure.

Various embodiments have been described with the aid of embodiments shown in the drawings. However, the present disclosure is to be understood as not being limited to the embodiments shown and described, since various modifications can be made to the embodiments without departing from the teaching underlying the instant disclosure. Therefore, the scope of protection is defined by the appended claims.

The invention claimed is:

1. A method for inspecting an intraocular lens for an unacceptable semi-opaque defect in a lens body thereof, the method comprising:
   illuminating, with laser light generated by a laser diode positioned on one side of the intraocular lens, the lens body of the intraocular lens in an area bounded by an edge of the lens body,
      wherein the laser light is directed to the one side of the intraocular lens;
   detecting, by a camera positioned on the one side of the intraocular lens, an intensity of laser light scattered by the illuminated lens body in a predetermined detection direction towards the camera,
      wherein the laser light is collected from the one side of the intraocular lens and the predetermined detection direction is different from a direction of reflection of the illuminating laser light;
   comparing the detected intensity of the scattered laser light with a predetermined threshold intensity;
   determining a size of at least one coherent area in which the detected intensity of the scattered laser light is higher than the predetermined threshold intensity; and
   determining whether the size of the at least one coherent area is larger than a predetermined threshold size, wherein a semi-opaque defect in the lens body is detected if the size of the at least one coherent area is larger than the predetermined threshold size.

2. The method according to claim 1, wherein comparing the detected intensity of the scattered laser light with the predetermined threshold intensity comprises:
   converting the detected intensity of the scattered laser light to a detected grey scale value representative of the detected intensity of the scattered laser light;
   converting the predetermined threshold intensity to a threshold grey scale value representative of the predetermined threshold intensity; and
   comparing the detected grey scale value with the threshold grey scale value, wherein determining whether the size of the at least one coherent area is larger than a predetermined threshold size comprises determining the size of at least one coherent area in which the grey scale values are above the threshold grey scale value.

3. The method according to claim 2, wherein illuminating the lens body comprises illuminating the lens body with a laser beam impinging on a surface of the lens body only within bounds of the edge of the lens body, the laser beam having a stationary impingement profile covering an area of at least 80% of the area of the surface of the lens body.

4. The method according to claim 3, wherein the laser beam is collimated with an evenly distributed intensity, and wherein the stationary impingement profile is a circular profile having a diameter that is 5%-10% smaller than the diameter of the edge bounding the lens body.

5. The method according to claim 3, wherein the stationary impingement profile of the laser beam has a shape of a grid with rectangularly arranged grid lines, with an evenly distributed intensity along the grid lines.

6. The method according to claim 2, wherein illuminating the lens body comprises:

illuminating the lens body with a laser beam having an impingement profile on a surface of the lens body, the impingement profile on the surface of the lens body covering an area of less than 20% of the area of the surface of the lens body; and moving the impingement profile over the surface of the lens body along a predetermined path to sequentially illuminate different portions of the lens body.

7. The method according to claim 1, wherein illuminating the lens body comprises illuminating the lens body with a laser beam impinging on a surface of the lens body only within bounds of the edge of the lens body, the laser beam having a stationary impingement profile covering an area of at least 80% of the area of the surface of the lens body.

8. The method according to claim 7, wherein the laser beam is collimated with an evenly distributed intensity, and wherein the stationary impingement profile is a circular profile having a diameter that is 5%-10% smaller than the diameter of the edge bounding the lens body.

9. The method according to claim 7, wherein the stationary impingement profile of the laser beam has a shape of a grid with rectangularly arranged grid lines, with an evenly distributed intensity along the grid lines.

10. The method according to claim 1, wherein illuminating the lens body comprises:

illuminating the lens body with a laser beam having an impingement profile on a surface of the lens body, the impingement profile on the surface of the lens body covering an area of less than 20% of the area of the surface of the lens body; and moving the impingement profile over the surface of the lens body along a predetermined path to sequentially illuminate different portions of the lens body.

11. The method according to claim 10, wherein the laser beam is focused and the impingement profile is a circular spot, and wherein the circular spot is moved over the surface of the lens body along the predetermined path.

12. The method according to claim 10, wherein the impingement profile is a straight line, and wherein the straight line is moved over the surface of the lens body along the predetermined path, the predetermined path being normal to the straight line of the impingement profile.

* * * * *